(12) United States Patent
Goodrich

(10) Patent No.: US 6,241,658 B1
(45) Date of Patent: Jun. 5, 2001

(54) SUCTION RETRACTOR

(76) Inventor: Harriet T. Goodrich, 40 Possum Trot La., Columbus, NC (US) 26622

( * ) Notice: Subject to any disclaimer, the term of this patent is extended or adjusted under 35 U.S.C. 154(b) by 0 days.

(21) Appl. No.: 09/615,012

(22) Filed: Jul. 12, 2000

(51) Int. Cl.[7] .................................................. A61B 17/02
(52) U.S. Cl. .......................................... 600/210; 600/205
(58) Field of Search ..................................... 600/210, 205

(56) References Cited

U.S. PATENT DOCUMENTS

| D. 320,658 | 10/1991 | Quigley et al. ............... D24/135 |
| D. 343,235 | 1/1994 | LeVahn ............................ D24/135 |
| D. 343,236 | 1/1994 | Quigley et al. ............... D24/135 |
| D. 359,118 | 6/1995 | Nates ............................... D24/112 |
| D. 412,984 | 8/1999 | Cover et al. ..................... D24/129 |
| 1,613,373 | * 1/1927 | Beck ................................. 600/205 |
| 1,972,391 | * 9/1934 | Morse .............................. 600/211 |
| 2,482,116 | * 9/1949 | Lanahan ......................... 600/205 |
| 2,672,859 | * 3/1954 | Jones .............................. 600/205 |
| 3,626,471 | * 12/1971 | Flourin ........................... 600/205 |
| 3,768,477 | * 10/1973 | Anders et al. ................. 600/205 |
| 3,998,217 | 12/1976 | Trumbull et al. . |
| 4,049,000 | * 9/1977 | Williams ........................ 600/210 |
| 4,226,228 | * 10/1980 | Shin et al. ...................... 600/210 |
| 4,232,660 | * 11/1980 | Coles .............................. 600/210 |
| 4,562,832 | * 1/1986 | Wilder et al. .................. 600/210 |
| 4,616,633 | * 10/1986 | Garcia ............................ 600/210 |
| 4,971,038 | 11/1990 | Farley . |
| 5,159,921 | 11/1992 | Hoover . |
| 5,248,297 | 9/1993 | Takase ............................ 604/22 |
| 5,656,027 | 8/1997 | Ellingboe ....................... 604/49 |
| 5,755,660 | 5/1998 | Tyagi .............................. 600/205 |
| 5,762,606 | 6/1998 | Minnich ......................... 600/205 |
| 5,779,649 | 7/1998 | Herbert .......................... 600/571 |
| 5,782,795 | 7/1998 | Bays ............................... 604/22 |

* cited by examiner

Primary Examiner—Paul J. Hirsch
(74) Attorney, Agent, or Firm—Joseph T. Guy; Hardaway/Mann IP Group; Nexsen Pruet Jacobs & Pollard, LLC

(57) ABSTRACT

Provided is a suction retractor for use in surgical procedures. The suction retractor comprises a handle wherein the handle comprises a couple for attachment to a suction tube. A retractor plate is contiguous to the handle and a retractor blade is contiguous to the retractor plate. The retractor blade further comprises a plurality of suction ports. A continuous channel interior to the handle, retractor plate and retractor blade connects the couple to the plurality of suction ports.

19 Claims, 4 Drawing Sheets

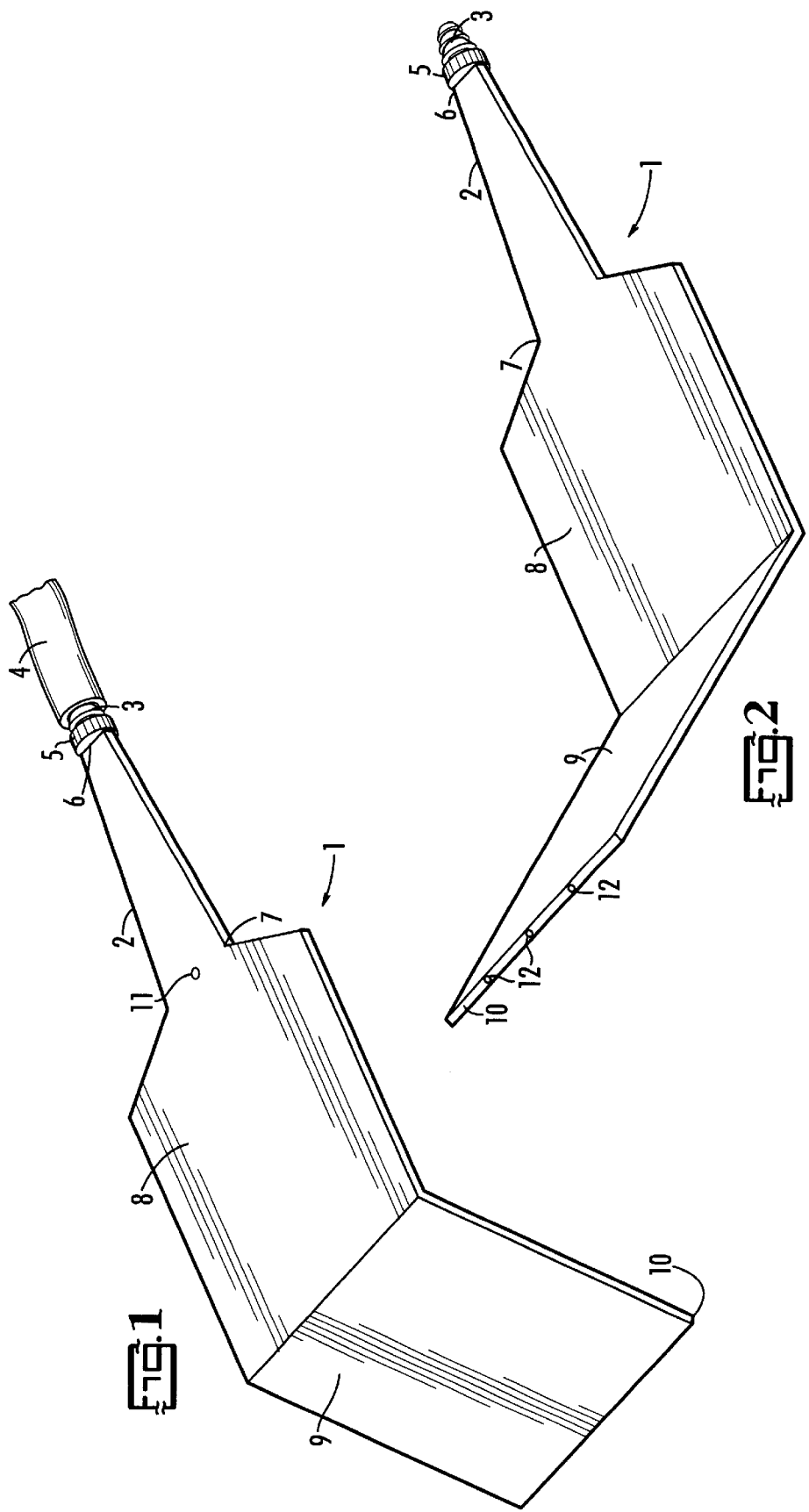

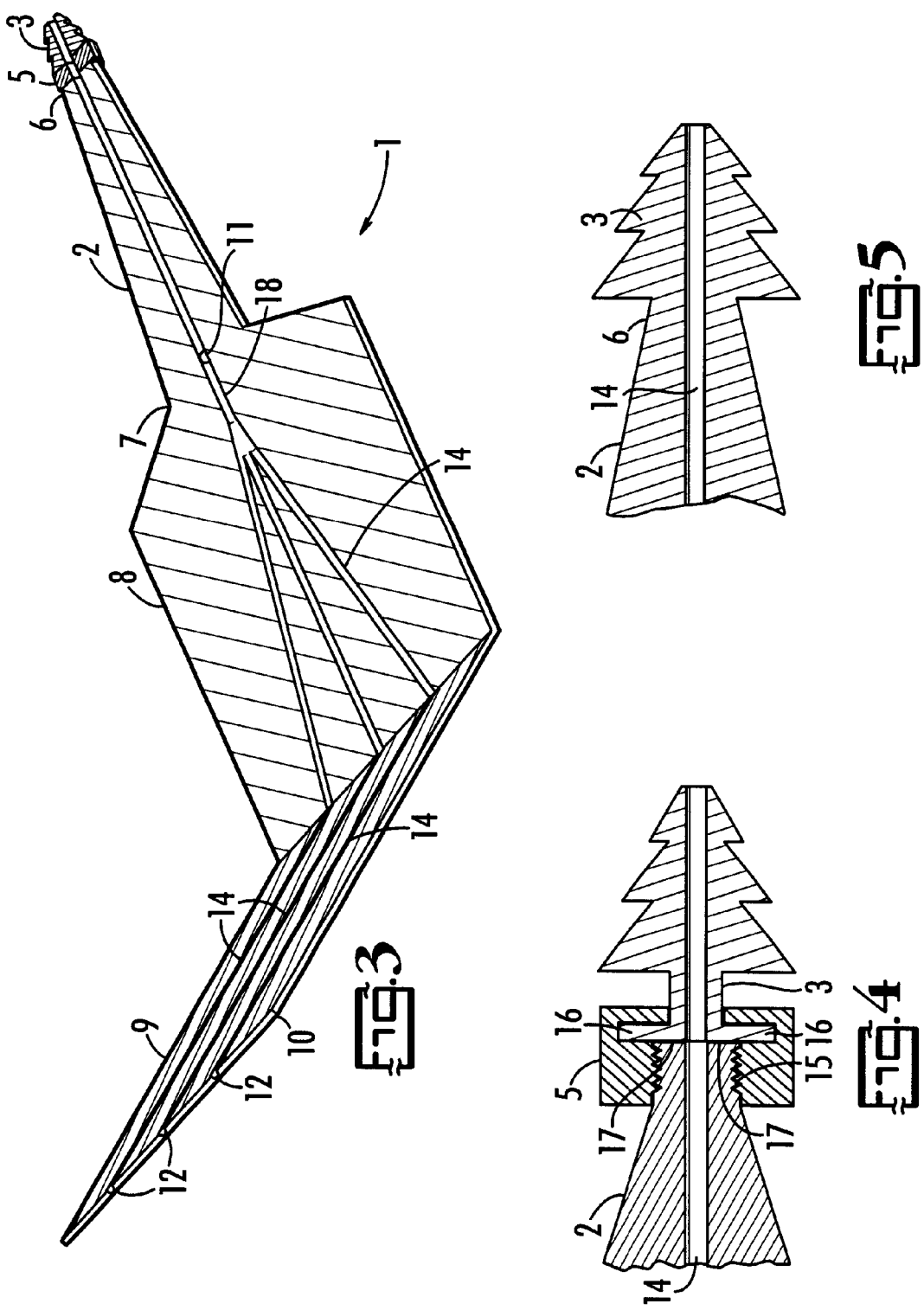

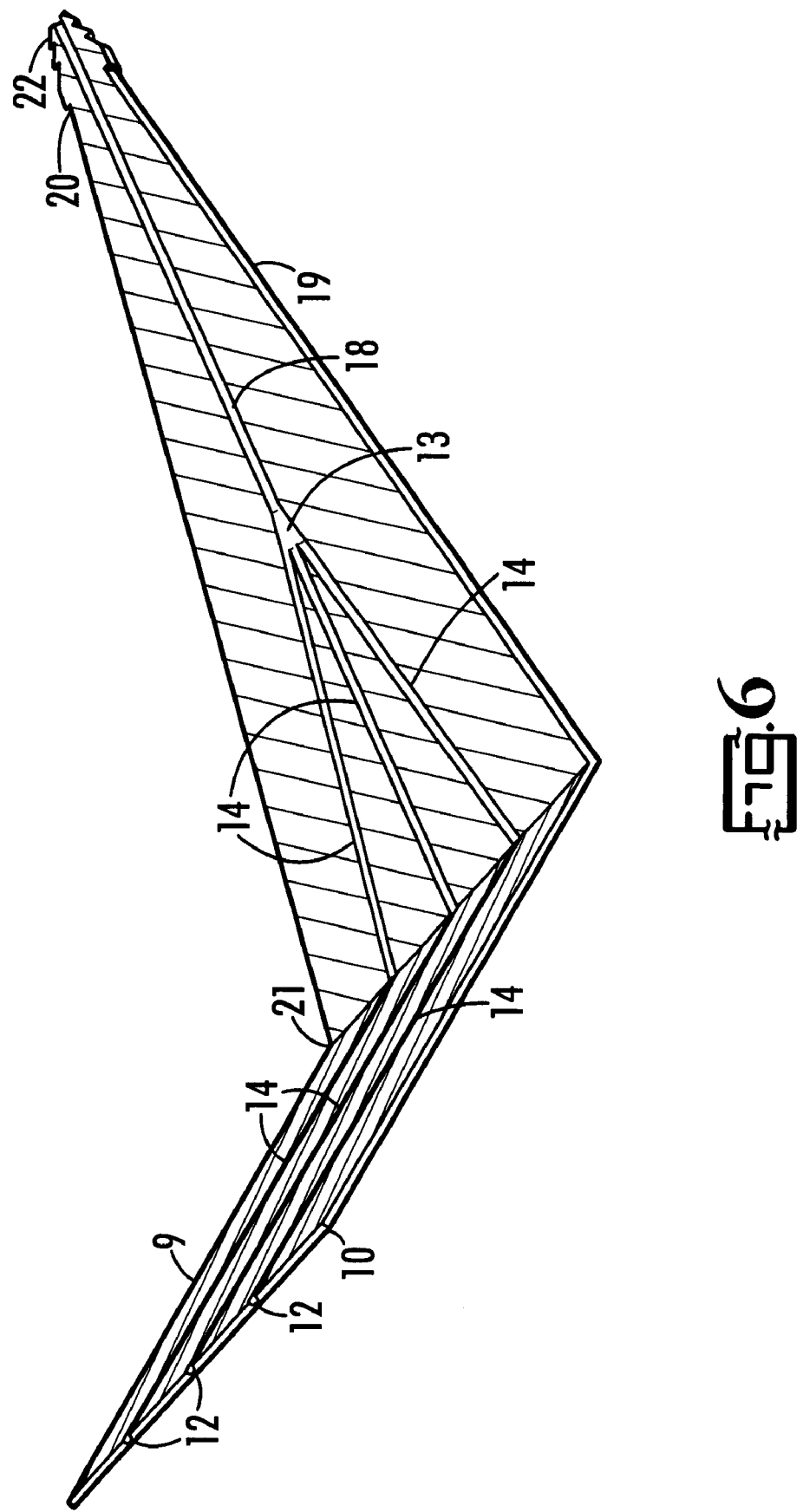

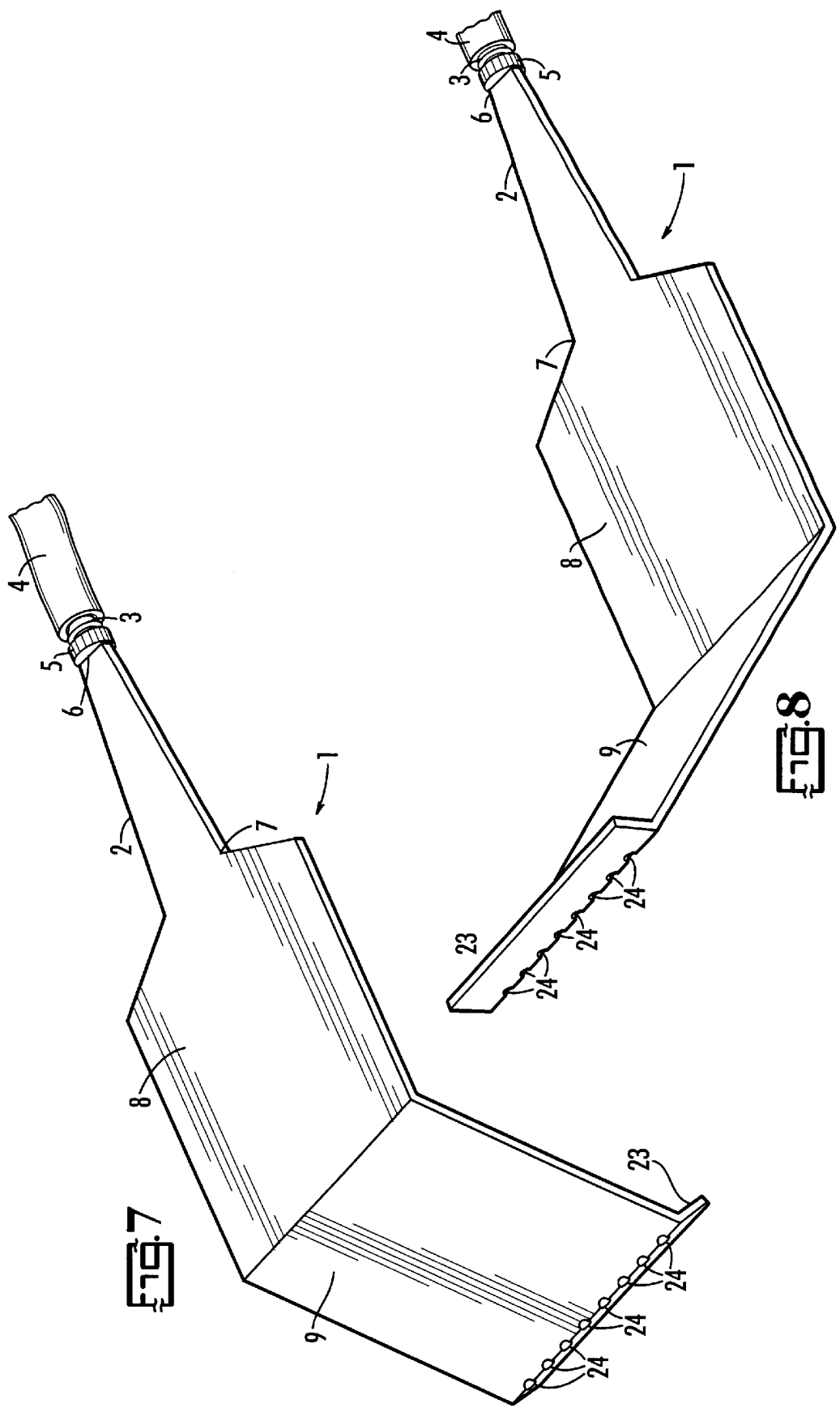

SUCTION RETRACTOR

FIELD

This invention is related to a medical device and more specifically to a medical retractor with a suction device integral thereto.

BACKGROUND

It is a common goal in modern surgical procedures to perform operations with the minimal level of invasion possible. It is a well documented observation that recovery time, patient discomfort and medical expense all decrease with minimally invasive medical procedures. It is therefore an ongoing goal to minimize the size of the incision necessary for surgery. One limitation to furthering the minimization of the incision for many surgical procedures, particularly those involving the abdomen, is the necessity to create an incision which is sufficiently large to allow the surgeon to adequately access the surgical site without compromising the field of view and without the surgeon being hindered by complicated apparatus which limit the ability of the surgeon to access the surgical area.

In a typical abdominal procedure an incision is made and the various tissue is retracted by a rigid device as shown and described, for example, in U.S. Pat. Nos. 3,998,217; 4,971,038; D320,658; D343,235 or D343,236. In addition to the retractor, which necessarily breeches the surgical area, various equipment must be available in, and near, the surgical site including a surgical knife such as a scalpel or laser, a light source, irrigation and Suction equipment etc. It has been a long felt desire to eliminate or consolidate surgical equipment without compromising the ability of the surgeon to perform an operation.

Examples of consolidated surgical equipment are provided in, for example, U.S. Pat. No. 5,159,921 wherein described is a flexible compartment which can be formed to various shapes as described. While this device has certain advantages, the size prohibits use in minimally invasive surgery due to the thickness of the device. U.S. Pat. No. 5,755,660 describes a surgical retractor wherein a suction apparatus is fixed to the outer portion of the retractor. This apparatus is undesirable since the suction device abuts into the field of view and the tubing breaches the surgical area which can be a burden to the surgeon and attendants.

There has been a long felt need in the art for a retractor with a suction device integral thereto which does not require the incision to be enlarged and which does not interfere with the operation.

SUMMARY

It is an object of the present invention to provide an improved suction retractor.

It is another object of the present invention to provide a medical device which assist in minimally invasive procedures.

A particular feature of the present invention is the simplicity in use and the minimization of tools required in and around an incision.

These and other features, as will be apparent, are provided in a suction retractor for use in surgical procedures. The suction retractor comprises a handle wherein the handle comprises a couple for attachment to a suction tube. A retractor plate is contiguous to the handle and a retractor blade is contiguous to the retractor plate. The retractor blade further comprises a plurality of suction ports. A continuous channel interior to the handle, retractor plate and retractor blade connects the couple to the plurality of suction ports.

Yet another embodiment is provided in a suction retractor for use in surgical procedures. The suction retractor comprises a handle wherein the handle comprises a couple for attachment to a suction tube. A retractor blade is attached to the handle and the retractor blade comprises a plurality of suction ports. A continuous channel is interior to the handle and the retractor blade and the continuous channel connects the couple to the plurality of suction ports.

Yet another embodiment is provided in a suction retractor for use in surgical procedures. The suction retractor comprises a handle wherein the handle comprises a couple for attachment to a suction tube. A retractor plate is contiguous to the handle. The suction retractor further comprises a retractor blade wherein the retractor blade comprises at least two suction ports and no more than eight suction ports. The retractor blade and retractor plate form an obtuse angle. The suction retractor further comprises a continuous channel interior to the handle, the retractor plate and the retractor blade wherein the continuous channel connects the couple to the plurality of suction ports.

BRIEF DESCRIPTION OF THE DRAWINGS

FIG. 1 is a top side view of an embodiment of the suction retractor.

FIG. 2 is a bottom side view of the embodiment shown in FIG. 1.

FIG. 3 is a cutaway view of the embodiment of FIG. 1 illustrating the channel and manifold of the suction retractor.

FIG. 4 is a cutaway partial of a preferred embodiment illustrating the attachment of the suction tube to the handle.

FIG. 5 is a cutaway partial view of a preferred embodiment illustrating a suction tube and its attachment.

FIG. 6 is a cutaway view of an embodiment illustrating the channel of the suction retractor.

FIG. 7 is a top side view of an embodiment of the suction retractor.

FIG. 8 is a bottom side view of the embodiment shown in FIG. 7.

DETAILED DESCRIPTION

An embodiment of the suction retractor will be described in reference to FIGS. 1, 2 and 3.

The suction retractor, generally represented at 1, comprises a handle 2, by which the suction retractor can be held and used. The handle is preferably planar due to lower cost associated with a planar shape but other shapes are contemplated including rounded, semicircular, or polygonal. A rounded handle with protrusions thereon to form a grip is contemplated in the present invention but this embodiment is less desirable due to the excess material required for manufacture. Attached to a back end, 6, of the handle, 2, is a couple, 3, for attaching a suction tube, 4. The couple may be attached with a threaded member, 5, as further described herein. The front end, 7, of the handle, 2, is contiguous with an optional, but preferred, retractor plate, 8, which imparts strength to the suction retractor and prohibits rotational distortion of the suction retractor during use. The retractor plate and handle may be combined in a single unit if so desired. Opposite to the handle and contiguous to the retractor plate, 8, is a retractor blade, 9. The retractor plate, 8 and retractor blade, 9, are each preferably planar and the retractor plate and retractor blade preferably form an obtuse angle there between. An obtuse angle is preferred since with an acute angle the lower edge, 10, of the retractor blade, 9, would be in forced contact with the patient as the tissue is retracted and therefore may cause trauma to the contacted area.

A plurality of suction ports, 12, in the lower edge, 10, are connected to the vacuum source by a continuous channel. The continuous channel preferably comprises a primary channel, 18, which connects to the couple, 3. The primary channel, 18, connects with a manifold, 13, as shown in FIG. 3. The manifold, 13, further connects to a plurality of secondary channels, 14, each of which terminates and is integral with a suction port, 12, thereby completing a continuous connection between the suction ports and the couple, 3. The primary channel, 18, manifold, 13, and secondary channels, 14, taken together foli a continuous channel which traverses and is interior to the retractor blade, 9, retractor plate, 8, and handle, 2. In operation suction is applied to the continuous channel by attachment of the suction tube, 4, to the couple, 3. The suction creates a pressure differential in the immediate vicinity of the suction ports, 12, whereby fluids are withdrawn into the channel and exit via the suction tube. The continuous channel formed by the primary channel, manifold and secondary channels are within the body of the suction retractor. At lease two ports are preferred to insure that adequate suction is provided to the surgical site. The maximum number of suction ports depends, in part, on the width of the retractor and the intended use. If the number of suction ports is to large then the pressure differential which can be established at each suction port becomes low which causes the operation to be low and the device becomes more easily clogged. It is most preferred that the number of ports does not exceed 8 and more preferred that the number of ports does not exceed 5. Most preferred is a suction retractor with 3 ports.

An optional release port, 11, is provided in the handle, 2, to break the vacuum and therefore cease the suction of fluids. The release port, 11, preferably forms a leak channel between the primary channel, 14, and the surface of the handle, 2, as illustrated in FIGS. 1 and 3. In use, the attendant would hold the suction retractor such that a finger is positioned over the release port, 11. When suction is required at the suction ports, 12, the release port, 11, would be covered with a finger thereby decreasing the pressure in the continuous channel. If suction is no longer desired the attendant would remove the finger from the release port thereby causing room air to be withdrawn into the channel and removing suction from the suction ports, 12. In another embodiment the release port, 11, may form a leak channel between the manifold and the surface of the handle.

FIG. 4 illustrates an embodiment for attaching the couple, 3, to the suction retractor. In the embodiment illustrated in FIG. 4 the handle, 2, comprises threads, 15, which mate with threads in the threaded member, 5. The threaded member, 5, comprises a central void for the body of the couple to protrude through. The couple, 3, comprises a lip, 16, which mates with the terminal end, 17, of the handle, 2, and forms a seal as the threads of the threaded member are rotatably engaged with the threads of the handle. In this embodiment the couple can be removed for cleaning, or a different size couple used without changing the entire suction retractor.

FIG. 5 illustrates another embodiment wherein the back end of the handle, 6, and the couple, 3, are contiguous. This embodiment requires fewer parts and is therefore more economical to manufacture.

FIG. 6 illustrates another embodiment of the present invention. In FIG. 6 the handle, 19, and retractor blade, 9, are contiguous and form the preferred obtuse angle as described previously. The handle, 19, comprises a back end, 20, wherein attached thereto is a couple, 22. The handle further comprises a front end, 21, which is attached and contiguous with the retractor blade, 9. In the embodiment illustrated in FIG. 6 the continuous channel comprising a primary channel, 18, manifold, 13, and plurality of secondary channels, 14, is interior to and traverses the handle and retractor blade. The suction ports, 12, breach the lower edge, 10, of the retractor blade, 9.

FIGS. 7 and 8 illustrate another embodiment of the present invention wherein similarly numbered elements are as described previously. The embodiment illustrated in FIGS. 7 and 8 comprises an optional, but preferred, lip, 23, which is directed back towards the handle of the suction retractor generally referred to at 1. The lip, 23, assist in the retraction of blood vessels and other organs or assist in the retraction of the epidermis (not shown). The lip and retractor blade preferably form an obtuse angle. More preferably, the lip and retractor blade from an angle of approximately 130°. At the intersection of the retractor blade, 9, and the lip, 23, is a plurality of suction ports, 24, the operation of which is previously described.

The ports may further comprise an optional, but preferred, grid to discourage tissue from entering the port and clogging the device.

Couples are well known in the medical arts as a convenient device for attaching tubing to a medical instrument as a fluid supply source or as a source of suction. Couples are typically tapered with annular ribs, as illustrated, but Luer Locks and threaded couplings are also well known, contemplated and within the scope of the present invention.

The material of construction is consistent with those materials typically utilized for forming retractors and related medical devices. Specifically contemplated are stainless steel or any suitable medical grade material which can be sterilized for reuse or sterilized and stored for single use applications such as a disposable plastic or the like.

The size and width of the suction retractor is chosen based on the operation being performed and is consistent with the size and width of retractors currently available.

The suction retractor of the present invention has been described with particular emphasis on specific embodiments. The suction retractor of the present invention could be modified to interact with other devices currently known to those skilled in the art. Particularly contemplated are holes for attaching the suction retractor to a frame as illustrated, for example, in U.S. Pat. No. 3,998,217. Also contemplated are finger holes which facilitate the use of the suction retractor in some applications.

The description and drawings enable one with ordinary skill in the art to reproduce and use the device without research or the necessity for further elaboration. It would be apparent to one of ordinary skill in the art that many modifications, alterations and adaptations could be made without departing from the scope of the invention as set forth in the claims which follow.

What is claimed is:

1. A suction retractor for use in surgical procedures wherein said suction retractor comprises:
    a handle wherein said handle comprises a couple for attachment to a suction tube;
    a retractor plate contiguous to said handle;
    a retractor blade contiguous to said retractor plate wherein said retractor blade comprises a plurality of suction ports; and a continuous channel interior to said handle, said retractor plate and said retractor blade wherein said continuous channel connects said couple to said plurality of suction ports.

2. The suction retractor of claim 1 wherein said continuous channel further comprises a primary channel connected to said couple.

3. The suction retractor of claim 2 wherein said continuous channel further comprises a manifold connected to said primary channel.

4. The suction retractor of claim 3 wherein said continuous channel further comprises a plurality of secondary channels connecting said suction ports to said manifold.

5. The suction retractor of claim 1 wherein said retractor blade further comprises a lip contiguous to said retractor blade and opposite to said retractor plate.

6. The suction retractor of claim 5 wherein said suction ports are in said lip.

7. The suction retractor of claim 5 wherein said suction ports are located at an intersection between said lip and said retractor blade.

8. The suction retractor of claim 1 wherein said retractor blade and said retractor plate form an obtuse angle.

9. A suction retractor for use in surgical procedures wherein said suction retractor comprises:
   a handle wherein said handle comprises a couple for attachment to a suction tube;
   a retractor blade attached to said handle wherein said retractor blade comprises a plurality of suction ports; and
   a continuous channel interior to said handle and said retractor blade wherein said continuous channel connects said couple to said plurality of suction ports.

10. The suction retractor of claim 9 wherein said continuous channel further comprises a primary channel connected to said couple.

11. The suction retractor of claim 10 wherein said continuous channel further comprises a manifold connected to said primary channel.

12. The suction retractor of claim 11 wherein said continuous channel further comprises a plurality of secondary channels connecting said suction ports to said manifold.

13. The suction retractor of claim 12 wherein said retractor blade further comprises a lower edge and said suction ports breach said lower edge.

14. The suction retractor of claim 9 comprising at least 2 suction ports and no more than 8 suction ports.

15. The suction retractor of claim 9 wherein said retractor blade and said handle form an obtuse angle.

16. A suction retractor for use in surgical procedures wherein said suction retractor comprises:
   a handle wherein said handle comprises a couple for attachment to a suction tube;
   a retractor plate contiguous to said handle;
   a retractor blade wherein said retractor blade comprises at least two suction ports and no more than eight suction ports and wherein said retractor blade and said retractor plate form an obtuse angle; and
   a continuous channel interior to said handle, said retractor plate and said retractor blade wherein said continuous channel connects said couple to said suction ports.

17. The suction retractor of claim 16 comprising no more than 5 suction ports.

18. The suction retractor of claim 17 comprising 3 suction ports.

19. A suction retractor for use in surgical procedures wherein said suction retractor comprises:
   a handle wherein said handle comprises a couple for attachment to a suction tube;
   a retractor plate contiguous to said handle,
   a retractor blade contiguous to said retractor plate wherein said retractor blade comprises a plurality of suction ports; and
   a continuous channel interior to said handle, said retractor plate and said retractor blade wherein said continuous channel connects said couple to said plurality of suction ports wherein said retractor blade further comprises a lower edge and said suction ports breach said lower edge.

* * * * *